United States Patent [19]  [11] Patent Number: 5,049,146
Bringham et al.  [45] Date of Patent: Sep. 17, 1991

[54] BLOOD/GAS SEPARATOR AND FLOW SYSTEM

[75] Inventors: Richard L. Bringham, San Clemente; R. Scott Bell, Irvine, both of Calif.

[73] Assignee: Baxter International Inc., Deerfield, Ill.

[21] Appl. No.: 359,178

[22] Filed: May 31, 1989

[51] Int. Cl.$^5$ ............................................. A61B 19/00
[52] U.S. Cl. ........................................ 604/4; 604/406; 604/410; 422/47; 128/DIG. 3
[58] Field of Search ................. 422/47; 604/408, 409, 604/410, 4, 5, 6; 128/DIG. 3

[56] References Cited

U.S. PATENT DOCUMENTS

| | | | |
|---|---|---|---|
| 3,545,937 | 12/1970 | Rozhold et al. | 422/47 |
| 3,765,537 | 10/1973 | Rosenberg | 210/446 |
| 3,827,860 | 8/1974 | Burlis | 422/47 |
| 3,853,479 | 12/1974 | Talonn et al. | 422/46 |
| 3,892,534 | 7/1975 | Leonard | 422/47 |
| 3,915,650 | 10/1975 | Talonn et al. | 422/47 |
| 3,918,912 | 11/1975 | Talonn et al. | 422/47 |
| 3,993,461 | 11/1976 | Leonard et al. | 55/178 |
| 4,033,345 | 7/1977 | Sorenson et al. | 604/4 |
| 4,035,304 | 7/1977 | Watanabe | 210/317 |
| 4,466,888 | 8/1984 | Verkaart | 210/232 |
| 4,493,705 | 1/1985 | Gordon et al. | 604/122 |
| 4,643,713 | 2/1987 | Viitala | 604/4 |
| 4,705,497 | 11/1987 | Shitaokoshi et al. | 604/4 |
| 4,734,269 | 3/1988 | Clarke et al. | 422/310 |

FOREIGN PATENT DOCUMENTS

| | | | |
|---|---|---|---|
| 193071 | 11/1957 | Austria . | |
| 0253467 | 7/1987 | European Pat. Off. | 19/2 |
| 2654725 | 6/1977 | Fed. Rep. of Germany . | |
| 2730420 | 2/1978 | Fed. Rep. of Germany . | |

Primary Examiner—Robert A. Hafer
Assistant Examiner—Kerry Owens
Attorney, Agent, or Firm—Michael C. Schiffer; Robert B. Buyan; Richard L. Myers

[57] ABSTRACT

A blood reservoir is formed with a hard outer shell housing defining at least one blood compartment. A flexible bag is mounted in the outer shell and is connected to the reservoir inlet port to allow blood to directly enter the flexible bag. The bag includes two oppositely positioned ends, one of which includes a mircoporous screen and is situated to lie partially below a minimum level attained by blood in the reservoir. The second bag end is substantially open, and includes a porous element partially coated with an antifoaming agent. The coated portion of the element is positioned above a maximum level attained by the blood in the hard shell. The potential of excessive mixing between the blood and air is reduced by controlling the expansion of the bag during blood flow.

59 Claims, 4 Drawing Sheets

BLOOD/GAS SEPARATOR AND FLOW SYSTEM

BACKGROUND OF THE INVENTION

The present invention is concerned with blood reservoirs, and in particular venous and cardiotomy blood reservoirs.

Many surgical procedures require that the patient's blood be diverted outside the body. For example, during open heart surgery the patient's blood must be directed around the heart and lungs. This usually involves the set up of an extracorporeal circuit. Extracorporeal circuits generally include devices for performing various tasks on the blood, e.g. oxygenation, filtration, and storage. Other procedures requiring the routing of blood through an extracorporeal circuit include extracorporeal membrane oxygenation (long term support) and autotransfusion.

Extracorporeal circuits are typically set up by an individual known as a perfusionist. The perfusionist controls the rate of blood flow and operates the various devices connected in the circuit. Extracorporeal circuits generally include oxygenators, heat exchangers, and filters, which are interconnected by surgical tubing. These circuits also include reservoirs. A blood reservoir is an enclosure into which blood is temporarily stored. The storage of blood in reservoirs allows regulation of the patient's blood volume and pressure. Typically, reservoirs also include various elements to filter and defoam the blood.

Blood flowing through an extracorporeal circuit, and particularly through the oxygenator and filters, may entrap air in the form of fine bubbles. Any gas bubbles must be removed from the blood prior to reintroduction into the patient.

Reservoirs are generally of two types. A first type of reservoir, known as a closed reservoir, is one which is formed from a generally flexible bag or container. Blood will expand this type of reservoir as it enters the reservoir. The air to blood interface is limited by the lack of empty space in the reservoir prior to filling with blood. Generally such reservoirs are sealed from the external environment. Closed reservoirs have numerous advantages. Such reservoirs isolate the blood from air thus limiting the extent of the blood to air interface which is detrimental to blood components. Flexible containers collapse and expand as the quantity of blood varies without delivering large quantities of air downstream into the extracorporeal circuit. This reduces potential injury to the patient from air embolism, particularly when all of the blood is removed from the reservoir.

The use of a flexible shell is also a benefit with oxygenators. For example, see U.S. Pat. No. 3,545,937, issued to Rozhold et al on Dec. 8, 1970; U.S. Pat. No. 3,827,860, issued to Burlis on Aug. 6, 1974; U.S. Pat. No. 3,853,479, issued to Talonn et al on Dec. 10, 1974; U.S. Pat. No. 3,892,534, issued to Leonard on July 1, 1975; U.S. Pat. No. 3,915,650, issued to Talonn et al on Oct. 28, 1975; and U.S. Pat. No. 3,918,912, issued to Talonn et al on Nov. 11, 1975.

One disadvantage with closed reservoirs is the inability to separate gross amounts of incoming air. The separation of small amounts of air from the blood is also difficult with closed reservoirs absent screen filters. It is also difficult to remove any entrapped air from the reservoir without physically compressing the bag, or by sucking or pumping the air out of the bag with a syringe or similar device.

A second type of reservoir is known as an open reservoir, and is formed from a rigid or hardshell container. The reservoir is filled with air which is pushed out by the entering blood. Usually a large portion of the air is removed during the priming process, but a small volume of the reservoir remains filled with air during the operation of the reservoir. This provides for an air to blood interface, which as stated may lead to the damage of various blood components.

One major advantage with open reservoirs is the establishment of the air to blood interface. Any air present in the incoming blood normally rises upwards through the blood passing across the blood to air interface. Such reservoirs typically include filters and defoaming elements which further enhance the release of entrapped gas across the blood to air interface. The released air is vented to atmosphere. Unlike closed reservoirs, open reservoirs allow for a precise measurement of the blood volume. That is, unlike the expanding and contracting closed reservoirs, open hardshell reservoirs allow for visual inspection of the quantity of blood flowing through the reservoir. By providing the hardshell reservoir with visually readable volume markings the precise amount of blood can be ascertained during the surgical procedure.

Open reservoirs also tend to impose a lower back pressure on the extracorporeal circuit. That is, blood flow through the reservoir will not increase the back pressure in the upstream portion of the circuit. Closed reservoirs induce a greater back pressure in the upstream portion of the circuit which may increase the amount of blood forced into the heart.

As stated, entrapped gas bubbles will rise in the reservoir and pass across the air to blood interface. Even though less efficient than open reservoirs, some entrapped air passes across this interface in closed reservoirs. To facilitate the removal of this gas, reservoirs have been designed with air vents. The air escapes to the environment through these vents. An example of a blood reservoir having an air vent is disclosed in U.S. Pat. No. 4,643,713, issued to Viitala on Feb. 7, 1987.

Examples of flexible shell reservoirs are disclosed in many of the above patent references, while examples of hardshell reservoirs are found in some commercially available oxygenators, such as the BCM-7, a product manufactured and sold by the Baxter Healthcare Corporation, Deerfield, Ill., Capiox E. an oxygenator sold by Terumo Corporation, Tokyo, Japan; and the CML, an oxygenator sold by Cobe Corporation, Boulder, Colo.

Blood passing through an extracorporeal circuit will usually entrap smaller air bubbles which normally will not pass through the air to blood interface. Some reservoirs have been designed to promote the breakdown of these smaller gas bubbles by incorporating screens in the blood pathway. For examples of such reservoirs see U.S. Pat. No. 4,493.705, issued to Gordon et al on Jan. 15, 1985, and U.S. Pat. No. 4,734,269, issued to Clarke et al on Mar. 29, 1988. These reservoirs include 100 to 250 microns and 50 to 300 microns, respectively.

Screens have also been positioned in filtering bags. These bags are usually positioned at the upstream end of extracorporeal circuits, and filter out denatured blood components. Entrapped gas bubbles would be broken down passing through this filter bag assembly. An example of such a bag is disclosed in U.S. Pat. No. 4,035,304, issued to Watanabe on July 12, 1977.

It is also known that during the oxygenation process, particularly with bubble oxygenators, the mixing of gas and blood forms foam. Foam is highly undesirable. While the foam may be merely removed from the circuit, it is the usual practice to separate any blood from the foam first. This is usually accomplished by passing the foam through a porous element which is at least partially coated with a defoaming substance, such as silicone antifoam.

Reservoirs have been designed to include fiber or equivalent elements which are coated with this antifoam material. Silicone antifoam or a derivative compound, breaks foam down into blood and gas. The gas is usually vented to the environment. An example of such a reservoir is seen in U.S. Pat. No. 4,466,888, issued to Verkaart on Aug. 21, 1984.

One disadvantage with the use of silicone antifoam, or equivalent substance, is the detrimental effect on blood. This material can become dislodged and shed into the blood. The shed antifoam material can become lodged in the patient's vascular system disrupting blood flow. Some researchers have suggested a mechanism for limiting the potential exposure of blood with silicone antifoam. Specifically, a reservoir, in combination with an oxygenator, is disclosed in U.S. patent application Ser. No. 338,347 filed Apr. 12, 1989, which is a continuation of U.S. Ser. No. 885,963, and assigned to the same assignee as the instant application. This application also discloses a reservoir having a defoaming material generally positioned above the maximum blood level. As stated in this application, the positioning of the defoaming material above this maximum blood level reduces the potential contact between the blood and the material.

It is thus apparent that both flexible and hard shell reservoirs provide distinct advantages, but also possess separate and distinct disadvantages.

SUMMARY OF THE INVENTION

The present invention overcomes the above discussed disadvantages by providing an open reservoir incorporating the benefits of both hard and flexible shells. Specifically, the reservoir of the invention includes a hardshell housing which defines at least one blood compartment. This compartment remains substantially open to the atmosphere. A flexible bag is fixed in this compartment, and is connected to the blood inlet.

The flexible bag is fixed in the compartment to allow for limited expansion. A first end of the bag is formed with a microporous screen and is situated in the hardshell to lie partially below a minimum blood level. A second bag end is formed to remain substantially open, and is positioned to lie above a maximum blood level in the hard shell. A porous body or mat is positioned at least partially in the bag second end. This body or mat is partially coated with a defoaming substance.

The blood entering the reservoir flows into and expands the flexible bag. The blood flows downward through and out the microporous screen in the lower end. The placement of the lower end below the minimum blood level ensures that blood exiting the screen will not excessively mix with any air. Foam entering the bag rises upward and is brought into contact with the defoaming material coated porous body. The placement of this body above the maximum blood level reduces the potential of contact between the blood and defoaming substance. The reservoir of the invention thus possesses the advantages of a flexible shell, while retaining the advantages of a hardshell.

In another preferred embodiment, the reservoir includes two separate blood reservoir compartments. One compartment is formed as described above and functions as a venous reservoir. A second compartment functions as a cardiotomy reservoir. This reservoir is situated above the venous reservoir to allow for gravity flow from the cardiotomy to venous reservoirs. This latter compartment includes inlet and outlet ports, and a multilayered filter assembly through which passes the blood. This filter assembly includes a defoaming substance coated body or mat which is surrounded by a microporous filter. This assembly breaks down both small air bubbles and foam.

Still other preferred embodiments include an assembly for connecting the cardiotomy reservoir compartment to the venous reservoir compartment which reduces the passage of air from the former to the latter, and a design for the venous reservoir hardshell which is formed to provide easy reading and measurement of the quantity of blood in the venous reservoir compartment.

DESCRIPTION OF THE DRAWINGS

The present invention may be better understood and the advantages will become apparent to those skilled in the art by reference to the accompanying drawings, wherein like reference numerals refer to like elements in the several figures, and wherein.

DESCRIPTION OF THE PREFERRED EMBODIMENTS

The present invention is directed to open reservoirs, and specifically to open venous reservoirs. In accordance with one preferred embodiment, the venous reservoir is incorporated in a housing also having a cardiotomy reservoir.

The reservoir of the invention provides the benefits of both hard and soft shell reservoirs by mounting a flexible bag in a hardshell. The bags flexibility ensures that the blood does not excessively mix with air. This aspect of the invention is provided by designing the flexible bag so that the blood is directed downward through a lower microscreen portion that is positioned to discharge the blood partially below the minimum blood level in the reservoir. The flexible bag is further designed to include a defoamer coated membrane positioned above the maximum blood level in the reservoir.

By "minimum blood level" it is meant the lowest level in the reservoir to which the blood will normally rise under normal blood flow and operating conditions for the particular reservoir.

By "maximum blood level" it is meant the highest level in the reservoir to which the blood will normally rise under normal blood flow and operating conditions for the particular reservoir.

The importance of providing for the downward flow of blood out through the screen below the minimum blood level is to minimize the contact between flowing blood and air. The turbulence caused by the blood flowing out from the screen would, if the screen is exposed to the air, cause a mixing action between the blood and air. This is an unwanted occurrence.

The positioning of the defoamer coated membrane above the maximum blood level reduces the potential of contact between the blood and the defoamer coating. The positioning of defoamer coating above the maximum blood level is more fully described in co-pending U.S. patent application Ser. No. 338,347 filed 4/12/89, which is a continuation of U.S. Ser. No. 885,963, both of which are assigned to the same assignee of this application, with the disclosure pertaining to the positioning of defoaming substances above the maximum blood level being incorporated herein by reference.

The reservoir of the invention is useful as a venous or cardiotomy blood reservoir, and may have any suitable shape or configuration. For illustrative purposes the invention will be described with reference to a venous reservoir upon which is positioned a cardiotomy reservoir.

Figure 1:
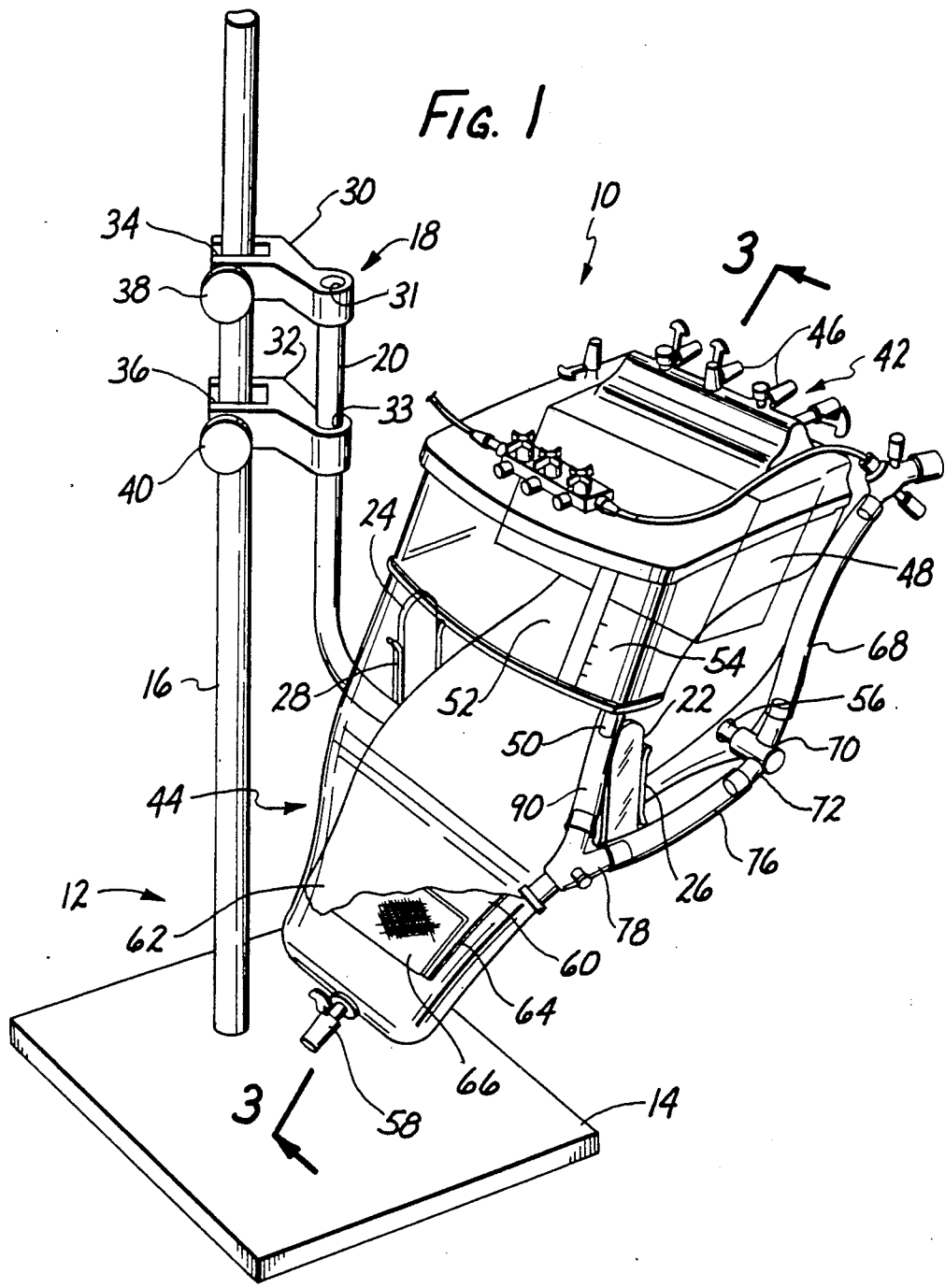
FIG. 1 is a prospective view of a reservoir mounted upon a stand in accordance with a preferred embodiment of the invention.
Figure 2:
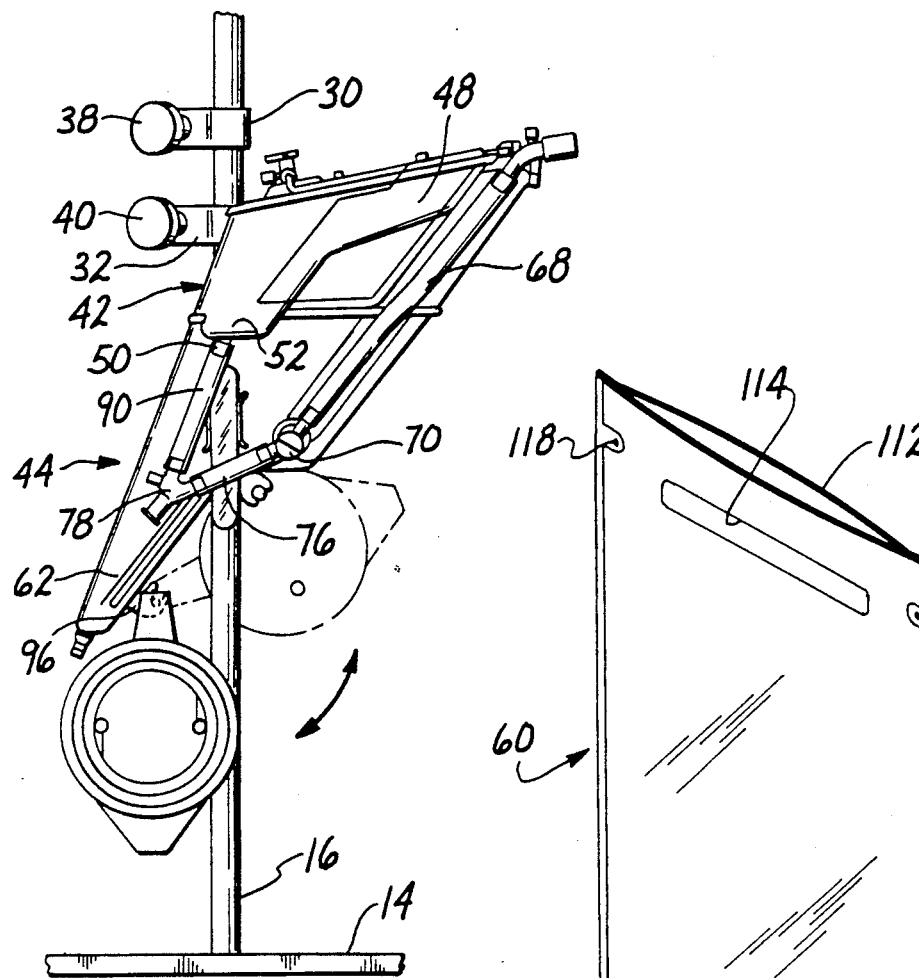
FIG. 2 is a side view of the reservoir of FIG. 1 additionally illustrating an oxygenator releasably connected to the bottom of the reservoir.

Referring now to FIGS. 1 and 2, a venous and cardiotomy reservoir assembly is seen generally at 10. The venous and cardiotomy reservoir assembly 10 is seen mounted upon a stand 12. Stand 12 includes a base portion 14 up from which extends a rod 16. The stand 12 further includes an arm assembly 18. The arm assembly 18 is formed to allow the reservoir assembly 10 to be positioned by the perfusionist at any desired height. Venous and cardiotomy reservoir assembly 10 is formed to be releasably mounted upon the arm assembly 18, with assembly 18 being formed to slide and lock down upon the rod 16.

Arm assembly 18 is formed from an L-shaped member 20. One side of member 20 includes two upwardly extending posts 22 and 24. These posts 22 and 24 are fixed to the member 20 to be snuggly positioned at opposite sides of the assembly 18. The posts 22 and 24 are dimensioned to slide in respective guides 26 and 28 formed on the side walls of the assembly 18. In this arrangement the reservoir assembly 10 is easily mounted to the arm assembly 18.

The arm assembly 18 is mounted to the L-shaped member 20 by two brackets 30 and 32. The two brackets 30 and 32 are formed with apertures 31 and 33 which slidingly fit about the member 20. Each bracket 30 and 32 also includes a slot 34 and 36, respectively. These slots 34 and 36 fit about the rod 16. Tightening screws 38 and 40 are threadably fit through the brackets 30 and 32 to engage and tighten down onto the rod 16.

As will be described more fully, the reservoir assembly 10 includes two separate reservoirs, cardiotomy reservoir and venous reservoir seen generally at 42 and 44, respectively. The cardiotomy reservoir 42 is formed to fit atop the venous reservoir 44. It should be noted that the two reservoirs 42 and 44 may be formed as a single integral unit, or as two completely separate devices.

Cardiotomy reservoir 42 includes multiple inlet ports 46. These ports 46 direct blood through a filter assembly seen generally at 48. Blood passing through the filter assembly 48 will fill the lower portion of the reservoir 42, seen generally at 52, which is formed with a well shaped region 100. As seen in FIG. 1, this portion of the reservoir 42 includes a gradient scale 54. The gradient scale 54 allows the perfusionist to determine the quantity of blood in the reservoir 42. Blood exits this reservoir 42 through outlet port 50.

Venous reservoir 44 includes a single inlet port 56 and a single outlet port 58. As will be described more fully herein, a flexible bag 60 is fixed in the venous reservoir 44 to a plate 62. This bag 60 includes a lower end 64 fitted with a microporous screen 66. The screen 66 has a porosity of from about forty to about two hundred microns, preferably one hundred microns. The small openings of the screen 66 ensure that small gas bubbles will not pass through the screen.

The opposite other end, not seen in FIG. 1, of the bag 60 is fitted with a porous element, also not seen in FIG. 1. The porous element is a foamed polyurethane structure. The desired porosity of this porous element is from about four hundred to about eighteen hundred microns. At least part of the porous element is coated with a defoaming substance, usually silicone antifoam.

Blood enters the venous reservoir through the inlet port 56, via a flexible tube 68 and connector assembly 70. Connector assembly 70 is mounted to the inlet port 56 and includes two tube connection stubs 72 and 74. The inlet port 56 is actually fitted into the side of the flexible bag 60. Blood enters the flexible bag 60 through the inlet port 56.

The connector assembly 70 functions to deliver venous blood from the patient, via the tube 68, and cardiotomy blood from the cardiotomy reservoir 42, via another flexible tube 76 to the flexible bag 60 mounted in the venous reservoir 44.

Figure 6:
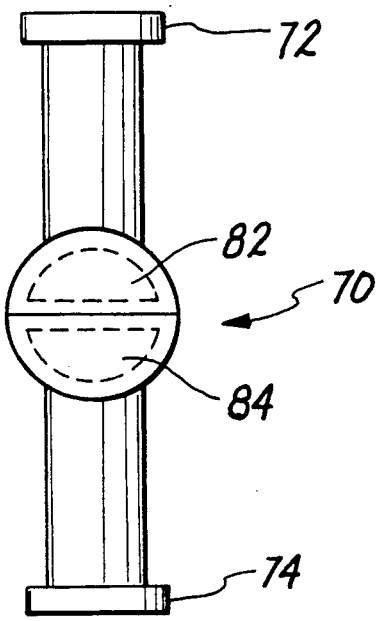
FIG. 6 is a side view of a connector assembly in accordance with an embodiment of the invention.

The connector assembly 70 is seen in greater detail in FIG. 6. This assembly 70 is coupled directly onto the inlet port 56. The assembly 70 defines a fluid pathway by an internal chamber, seen in phantom at 82. This chamber 82 is subdivided into two chambers by an internal wall, seen in phantom at 84. One half of the divided chamber 82 communicates with stub 72, while the other half with stub 74.

Figure 5:
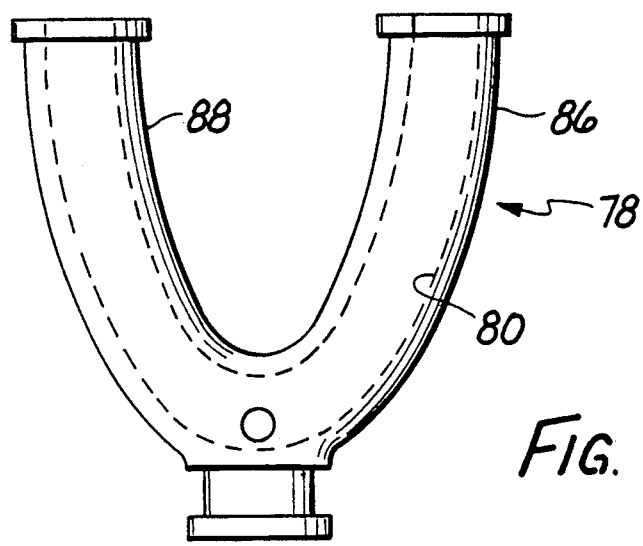
FIG. 5 is a side view of a Y-shaped connector in accordance with an embodiment of the invention.

The flexible tube 76 is further coupled to one arm 86 of a Y-connector 78, seen in FIG. 5. The Y-connector 78 includes a second arm 88 coupled to a further flexible tube 90, which is coupled to the outlet port 50 of the cardiotomy reservoir 42. As seen in FIG. 5, Y-shaped connector 78 further includes two access ports 92 and 94. These ports 92 and 94 allow either for the withdrawal of blood or access into the blood pathway by the connection of various devices to one of these ports.

The Y-connector 78 is formed with an internal fluid pathway 80. This pathway 80 is generally Y-shaped. The Y-connector 78 is coupled to the flexible tubes 90 and 76 to be positioned at an angle to impede the passage of gas. The purpose of providing the Y-shaped connector 78 is to limit the ability of gas passing through any of the tubes from entering the venous reservoir 44.

The positioning of the cardiotomy reservoir 42 above the venous reservoir 44 allows for gravity flow. The use of the flexible tubing to interconnect the outlet ports of the cardiotomy reservoir 42 to the inlet ports of the venous reservoir 44 provides a mechanism for interrupting and controlling the flow of blood between the reservoirs 42 and 44. Blood flow to the venous reservoir 44 can be interrupted by clamping off the associated flexible tubings 90 or 76. This allows for control of the flow of cardiotomy blood to the venous reservoir 44.

As seen in FIG. 2, the reservoir assembly 10, and specifically reservoir 44 is formed with hooks, one of which is seen generally at 96. These hooks 96 are disposed at the lower underside of the reservoir 44. An oxygenator of the type more fully described in co-pending U.S. patent application Ser. No. 260,164 filed Oct. 20, 1988, may be hung from these hooks 96. The outlet port 58 of the reservoir 44 may then be coupled to the inlet port of the oxygenator, not shown, to provide for transfer of the blood to the oxygenator.

Figure 3:
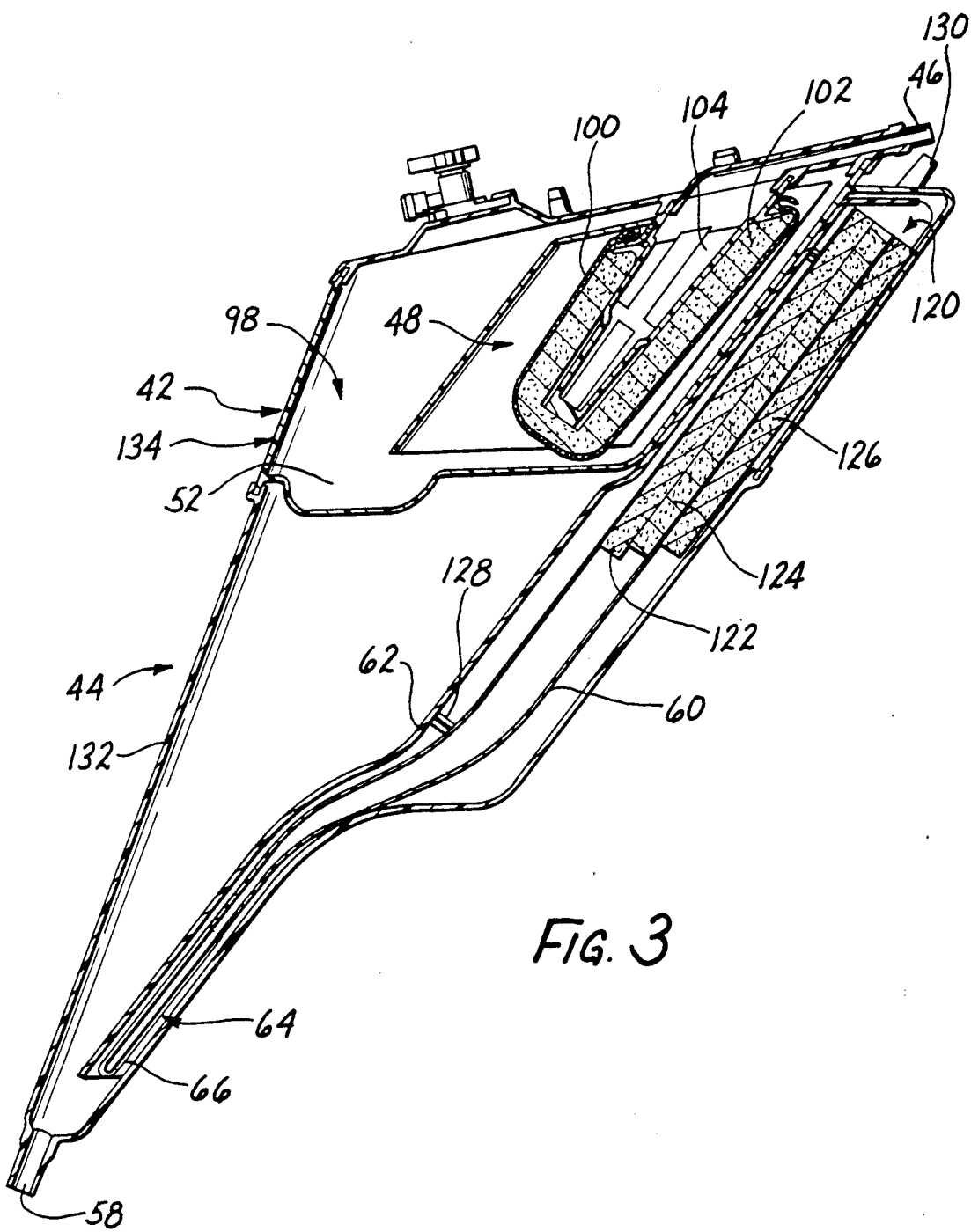
FIG. 3 is a cross-sectional view of the reservoir of FIG. 1 along line 3—3.

Referring now to FIG. 3, the components forming the reservoirs 42 and 44 will now be described in more detail. As stated, the reservoir assembly 10 includes two separate reservoirs, venous reservoir 44 and cardiotomy reservoir 42. These reservoirs 42 and 44 may either be integrally formed, or as illustrated, two separate housings assembled together. The cardiotomy reservoir 42 is situated on top of the venous reservoir 44.

The cardiotomy reservoir 42 contains the cardiotomy filter assembly 48 which is situated in a portion of the internal chamber defined in the cardiotomy reservoir 42. This internal chamber, seen generally at 98, is accessed via the cardiotomy inlet ports 46. Blood entering through these ports 46 travels first through the cardiotomy filter assembly 48 and then temporarily accumulates in the internal chamber 98.

The cardiotomy filter assembly 48 includes a porous filter element 100, a defoamer element 102, and a grid housing 104. The grid housing 104 is fixed to the cardiotomy filter assembly 48 to hang downward in the internal chamber 9B. The defoamer element 102 and porous filter element 100 are respectively secured about the grid housing 104. Generally the defoamer element 102 and porous filter membrane 100 are fixed about the grid housing 104 by a strap or band.

This grid housing 104 defines an internal region or inner blood receiving space, seen generally at 106, into which blood enters from the cardiotomy inlet ports 46. Numerous openings 108 are formed in the grid housing 104 through which blood passes into the defoamer element 102. Blood will then pass through the defoamer element 102 and then the porous filter element 100.

The defoamer element 102 is any suitable biocompatible material, typically a porous polyurethane foam. The porosity of this material is generally in the range of from about four hundred to about eighteen hundred microns. Cardiotomy blood typically contains blood components, bone and tissue fragments, entrapped gas bubbles and foam, which is a mixture of blood and gas bubbles. A defoamer coating is applied to the defoamer membrane 102. This defoaming coating, not shown, is usually silicone antifoam. The blood components and fragments become entrapped within the defoamer element 102. Larger gas bubbles are broken down as the blood passes through the defoamer element 102. Foam passing through the defoamer element 102 is at least partially broken down into gas and blood.

The smaller gas bubbles, generally in the range of twenty to one hundred microns, entrapped in the blood passing through the restricted passageways of the porous filter element 100 become broken down. The porous filter element 100 is generally prepared from a polyester felt material, and is mounted about the defoamer filter 102.

Blood exiting the porous filter membrane 100 travels down into a well 110 formed at the bottom of the cardiotomy reservoir 42. The cardiotomy outlet port 50 communicates with this well 110.

As stated above, the cardiotomy outlet port 50 is coupled through various tubes and connectors to the inlet port 56 of the venous reservoir 44. The arrangement of these various tubes and connectors, and particularly the design of Y-connector 78 minimizes the passage of gas bubbles into the venous reservoir 44.

Figure 4:
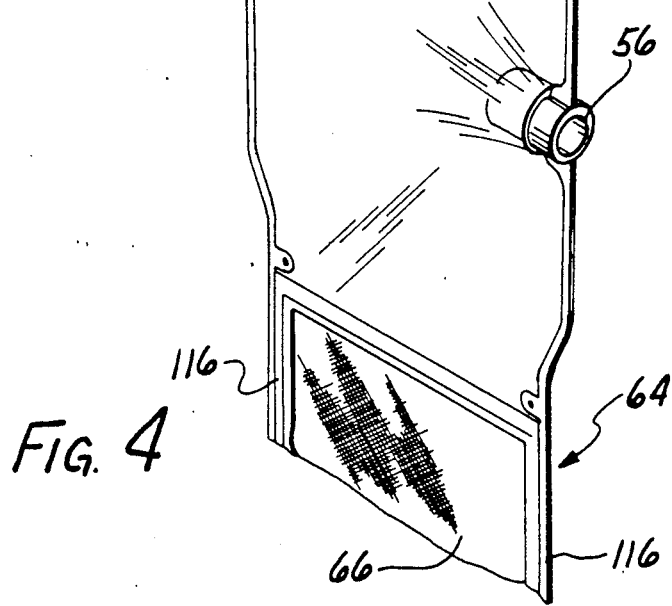
FIG. 4 is a rear prospective view of a flexible bag assembly of the reservoir of the invention.

The inlet port 56 is connected directly into the flexible bag 60, which is mounted to the bag support plate 62 in the venous reservoir 44. The bag is sealed below and partially around the inlet port 56 as seen in FIG. 4 at 55. This seal 55, which is generally linear in form, inhibits the backflow of air or blood through the inlet port 56. An illustration of a preferred design for the flexible bag 60 is seen in FIG. 4.

Flexible bag 60 is an elongated two walled structure formed by sealing the side edges of the two overlapping sheets of flexible material forming the flexible bag 60. The material from which the flexible bag 60 may be formed includes, polyvinyl chloride (PVC) and urethane. One end of the bag, seen at 112, remains unsealed and open. As will be described, this first open end 112 will be positioned at the upper end of the venous reservoir 44.

The flexible bag 60 is further formed with an open slot 114. This open slot 114 is positioned contiguous to the first open end 112. This open slot 114 will function as an overflow drain if the flexible bag 60 becomes filled with blood.

The inlet port 56 is fitted into the midpoint of the flexible bag 60. Typically, the inlet port 56 is formed by sealing a small tube between the two sheets of material forming the flexible bag 60. A small portion of the tube forming the inlet port 56 is positioned outside the flexible bag 60 to allow connection with the connector assembly 70.

As stated, that end of the flexible bag 60 opposite the first open end 112 includes a microporous screen 66. This screen is formed by folding a sheet of screen material and sealing this folded over sheet between the overlaid sheets forming the flexible bag 60. Generally, a rectangular shaped cut-away is formed at this end of the overlaid sheets forming the flexible bag 60 to define two strips 116 and 117. The folded over screen material is positioned and sealed between these strips 116 and 117. The remainder of the folded over screen material is then sealed to the sheets to define a lower accessible end of the flexible bag 60.

Blood entering the flexible bag 60 through the inlet port 56 travels downward and exits through the microporous screen 66. The porosity of this microporous screen 66 filters out the majority of any remaining gas bubbles. Generally, the microporous screen 66 is formed from a material having a porosity of from about forty to about two hundred microns, with the preferred material having a porosity of one hundred microns.

The flexible bag 60 is mounted in the venous reservoir 44 to the bag support plate 62. This is accomplished by forming the flexible bag 60 with a plurality of connector holes 118. These holes 118 are arranged so that when the flexible bag 60 is fixed to the bag support plate 62 the upper end of the flexible bag 60 is positioned higher than the microporous screen 66. The placement of the holes 118 also ensures that the first open end 112 is securely fixed to the bag support plate 62 in an open arrangement. The flexible bag 60 is fixed to the bag support plate 62 by pins, one of which is seen at 128.

The mid region of the flexible bag 60 is mounted to the bag support plate 62 at a location contiguous to the microporous screen 66. The flexible bag 60, which is fixed to the bag support plate 62, expands and contracts by the flowing blood. In this manner the blood is directed through the bag to the lower end defined by the microporous screen 66, while minimizing excessive mixing between the blood and the air.

The porosity of the microporous screen 66 restricts the passage of the blood into the remainder of the reservoir, causing the blood to fill a portion of the flexible bag 60 under normal blood flow rates, typically from about one to about seven liters per minute. Any foam entering the flexible bag 60 will rise upward towards the first open end 112. Further, any gas released from the blood travels upward and out of the flexible bag 60 through the first open end 112.

The venous reservoir 44 also includes a porous element which is at least partially coated with a defoamer coating, i.e. silicone antifoam. Preferrably, the entire porous element is coated with the antifoam substance. Referring to FIG. 3, this porous membrane is seen generally at 120, and may be formed from any suitable material, but typically is a polyurethane foam which has a porosity of from about four hundred to about eighteen hundred microns, preferably eight hundred fifty microns.

As illustrated, porous membrane 120 is multilayered, with two layers 122 and 124, situated inside the flexible bag 60, and one layer 126 positioned outside. All three layers 122, 124, and 126 are arranged above the inlet port 56. The external layer 126 may be formed by folding over a single sheet of the material forming the porous element 120, and placing a portion inside and outside of the flexible bag 60. The two inner layers 122 and 124 may be a single layer.

The various layers 122, 124 and 126 of the porous element 120 will also be positioned to cover the open slot 114. In the preferred embodiment the porous element 120 is coated at a position below the open slot 114 to ensure that the rising blood foam will be brought in contact with the antifoam material. As the blood foam level rises in the flexible bag 60 it passes into the porous element 120.

The placement in the venous reservoir 44 of the inlet port 56, open slot 114 and first open end 112, in combination with the porous element 120 provides that the portion of the porous element 120 which is coated with a defoaming coating will lie above the maximum blood level in the flexible bag 60. This positioning, and the added benefit of providing the flexible bag 60 with the open slot 114 ensures minimal contact between the blood and the defoaming coating. The advantages of providing for minimal contact between the defoaming coating and the blood are discussed more fully in co-pending U.S. patent application Ser. No. 338,347 filed Apr. 12, 1989, which is a continuation of U.S. Ser. No. 885,963, both of which are assigned to the same assignee of this application. The description in this reference to the desired positioning of the defoaming coating is incorporated herein by reference. Any blood exiting through the open slot 114 flows downward along the inside of the reservoir housing 132. Again, excessive mixing of the blood with air is avoided.

As the blood and foam passes through the porous element 120, including the coated portion, gas entrapped in the blood is released. This gas exits the flexible bag 60 through the first open end 112, and exits the venous reservoir 44 through one or more gas vents, one of which is seen at 130.

The placement of the bag support plate 62 in the venous reservoir 44 ensures a snug fit of the flexible bag 60. As seen in FIG. 3, the bag support plate 62 is positioned farther from the walls of the venous reservoir 44 at its upper end than at its lower end. This, in addition to the attachment of the flexible bag 60 to the bag support plate 62 allows for minimal expansion of the flexible bag 60. This also ensures that any foam entering the flexible bag 60 will rise upward and be brought into contact with the coated portion of the porous element 120. It is thus paramount that the flexible bag 60 be dimensioned to ensure adequate volume for blood below the coated porous element 120 under normal flow conditions. This establishes the defined maximum blood level in the particular venous reservoir 44.

The flexible bag 60 is fixed to the bag support plate 62 to position the microporous screen 66 at least partially below the minimum blood level for the particular venous reservoir 44. Further, the distance between the bag support plate 62 and the walls of the venous reservoir 44 ensure a tight fit for this section of the flexible bag 60. The positioning of the microporous screen 66 partially below the minimum blood level limits contact between blood and air.

Additionally the constraining of the expansion of the flexible bag 60 by placement of the bag support plate 62 in the venous reservoir 44 limits turbulence of the blood exiting through the microporous screen 66, which reduces excessive mixing between the blood and air, and also constrains excessive expansion of the bag limiting the volume of blood held with the bag during normal circulation. Blood exiting the microporous screen 66 flows into the bottom of the venous reservoir 44 and exits out of the venous reservoir outlet port 5B. The placement of the bag support plate 62 and the bag 60 lower end limits the formation of vortex blood flow exiting through the screen 66.

The reduction of contact and mixing between the blood and air reduces the potential of blood component damage in the form of red blood cell destruction (hemolysis), platelet depletion and/or activation and protein denaturation.

In accordance with a preferred embodiment, the venous reservoir 44 is formed with a gradient scale, not shown, which is visible from the front of the venous reservoir 44, seen generally at 132. The bag support plate 62 of this preferred embodiment is white to provide for better visibility of the gradient scale and level of blood.

A still further preferred embodiment is one in which the front face or forward wall 132 of the venous reservoir 44 is arranged at an angle to the floor to position the gradient scale and reservoir level for easy viewing by the perfusionist. As shown in FIG. 3, the rearward wall 133 of the reservoir 144 is closest to the forward wall 132 near the bottom and thereof and the forward wall 132 and rearward wall 133 become progressively further apart as they emanate upwardly from the bottom end of the reservoir 144. This placement of the venous reservoir 44 is accomplished by mounting the venous reservoir 44, and more particularly the reservoir assembly 10 to the stand 12 to position the front face 132 of the venous reservoir 44 at an angle of from about 60° to about 85°, preferably 70° to the floor.

A still further modification is to provide the cardiotomy reservoir 42 with a gradient scale upon its front face, seen generally at 134. To improve the visibility of this scale the grid housing 104 includes a plate assembly 136. This plate assembly 136 extends out from the grid housing 104 and angles downward to provide a solid surface behind the gradient scale disposed on the front face 134. Again, it is preferable if this plate assembly 136 be white.

While the preferred embodiments have been described, various modifications and substitutions may be made thereto without departing from the scope of the invention. Accordingly, it is to be understood that the invention has been described by way of illustration and not limitation.

What is claimed is:

1. A venous and cardiotomy blood reservoir comprising:
   a housing defining at least two separate compartments, with a second of said compartments being positioned above the first of said compartments, said housing including separate inlet and outlet ports communicating respectively with each of said compartments;
   connecting means coupled to said inlet ports of a first of said compartments and said outlet ports of a second of said compartments;
   a flexible bag means positioned in said housing first compartment for receiving blood through said inlet ports of said first compartment, said bag means being securely mounted in said compartment to restrict expansion of said bag means as said blood enters through said inlet ports, said bag means having a first end including a porous screen through which blood flows out of said bag means, and a second opposite end including a porous defoamer means which is at least partially coated with an antifoam material, with said partially coated portion being positioned above a maximum blood level in said reservoir;
   a porous element positioned in said second compartment between said inlet and outlet ports, said porous element being coated with an antifoaming material;
   a plate mounted in said housing to which said bag means is securely mounted along its edges;
   said first bag means end being positioned at a level to lie partially below a minimum blood level in said reservoir;
   said bag means being an elongated flexible bag which is mounted in said housing with said first end being positioned horizontally below said second end;
   said screen having a porosity of from about forty to about two hundred microns;
   said porous defoamer means having a porosity of from about four hundred to about eighteen hundred microns; and
   said connecting means comprising a tube fitting means which connects to said inlet port of said first compartment and a flexible tubing connected to said tube fitting means and said outlet port of said second compartment.

2. The blood reservoir of claim 1 wherein said tube fitting means is positioned in relation to said first compartment inlet means to limit the introduction of air into said first compartment.

3. The reservoir of claim 2 wherein bag means is fixed in said compartment to define a blood flow path traversing downward from said inlet to said outlet, whereby blood entering through said inlet travels under the influence of gravity to said outlet.

4. The reservoir of claim 3 further including means for mounting the reservoir to a stand, said mounting means orientating a forward facing wall of said reservoir at an angle to the floor upon which said stand rests allowing for examination of the contents of the reservoir.

5. The reservoir of claim 4 wherein said reservoir is mounted to a stand to position a forward wall of the reservoir at an angle of from about 60° to about 85° to said floor.

6. The reservoir of claim 4 wherein said reservoir is mounted to a stand to position a forward wall of the reservoir at an angle of about 70° to said floor.

7. A cardiotomy and venous blood reservoir device comprising:
   a rigid housing defining an upper compartment and a lower compartment therewithin;
   said upper compartment having a cardiotomy blood inlet, a cardiotomy blood outlet and a cardiotomy blood filter element disposed therein between the cardiotomy blood inlet and the cardiotomy blood outlet such that cardiotomy blood entering the upper compartment through the cardiotomy blood inlet will pass through said cardiotomy filter element prior to exiting the upper compartment through the cardiotomy blood outlet;
   said lower compartment having a flexible bag positioned therewithin, said flexible bag having a top end, a bottom end, a blood inlet, a blood outlet and a microporous screen element positioned between the blood inlet and the blood outlet such that blood entering the flexible bag through the blood inlet will pass through the microporous screen element prior to exiting the flexible bag through the blood outlet;
   the blood outlet of the flexible bag positioned within the lower compartment being located such that blood passing out of said blood outlet will collect inside of said lower compartment outside of said flexible bag;
   a blood outlet port formed in the bottom of the lower compartment below the bottom of said flexible bag to permit blood passing out of the flexible to subsequently drain out of the lower compartment.

8. The device of claim 7 wherein the cardiotomy filter element disposed within said upper compartment comprises:
   a porous filter element formed around and defining an inner blood receiving space adjacent said cardiotomy inlet such that blood flowing in the cardiotomy inlet will enter the inner blood receiving space and will subsequently pass outwardly through said porous filter element.

9. The device of claim 8 wherein said porous filter element comprises a polyester felt material.

10. The device of claim 7 further comprising:
    a defoamer element mounted within the upper chamber and interposed between the cardiotomy blood inlet and the cardiotomy blood outlet such that cardiotomy blood entering the upper chamber through the cardiotomy inlet will pass through the defoamer element prior to exiting the upper chamber through the cardiotomy blood outlet.

11. The device of claim 10 wherein said defoamer element comprises a quantity of porous foam material containing a chemical antifoam agent.

12. The device of claim 10 wherein said defoamer element and said porous filter element are both configured and disposed about an inner blood receiving space adjacent said cardiotomy blood inlet such that cardiotomy blood flowing in the cardiotomy blood inlet will initially pass into said inner blood receiving space and will subsequently pass outwardly through the defoamer element and the porous filter element.

13. The device of claim 10 wherein said defoamer element has a pore size of approximately 400–1800 microns.

14. The device of claim 10 wherein said defoamer element is formed of porous polyurethane foam.

15. The device of claim 7 wherein the flexible bag is positioned within the lower compartment such that blood exiting the outlet of the flexible bag will enter the lower compartment, outside of the flexible bag prior to passing out of the lower compartment through said blood outlet port.

16. The device of claim 7 wherein a minimum operational blood level in the lower compartment is known and wherein:
the flexible bag is positioned within the lower compartment such that the blood outlet of the flexible bag is beneath the minimum blood level in said lower compartment.

17. The device of claim 7 further comprising a plate mounted in the lower compartment to which said flexible bag is mounted.

18. The device of claim 17 wherein said plate is positioned in spaced relation to a first portion of said rigid housing and wherein said flexible bag is positioned between said plate and said first portion of the rigid housing such that expansion of said flexible bag is limited to the space existing between said plate and said portion of said rigid housing.

19. The device of claim 18 wherein the first portion of the rigid housing is the rearward wall of the lower compartment such that the bag is disposed between said plate and said rearward wall.

20. The device of claim 7 wherein the microporous screen element has a pore size of approximately 40–200 microns.

21. The device of claim 7 wherein:
the top end of said flexible bag is open; and
a second porous defoamer element is disposed within the top end of flexible bag such that foam rising within the flexible bag will contact said defoamer element prior to flowing out of the open top end of the flexible bag.

22. The device of claim 21 wherein said second porous defoamer element comprises:
at least a first mass of porous foam material positioned inside the flexible bag, adjacent the open top end thereof.

23. The device of claim 21 wherein said second porous defoamer element further comprises:
at least a second mass of porous foam material disposed outside of said flexible bag near the open top end thereof.

24. The device of claim 7 wherein the portion of said rigid housing defining said lower compartment comprises a forward wall and a rearward wall, opposing said forward wall, said forward wall and said rearward wall being closest to one another at the bottom end of said lower compartment and diverging away from one another thereabove.

25. The device of claim 24 wherein said device is mountable on a stand above a generally horizontal underlying floor such that the forward wall of the lower compartment is disposed at an angle of about 60–85 degrees relative to the underlying floor.

26. The device of claim 25 wherein the forward wall of the lower compartment is disposed at an angle of approximately 70 degrees relative to the underlying floor.

27. The device of claim 7 wherein said rigid housing is formed of clear plastic.

28. The device of claim 27 wherein a gradient scale is formed on the forward wall of the lower compartment to permit measurement of the level of blood within said lower compartment.

29. The device of claim 7 further comprising:
a connector for concomitantly fluidly connecting the blood inlet of the flexible bag within the lower compartment to (a) the cardiotomy blood outlet of the upper compartment and (b) a separate venous return source, thereby permitting filtered cardiotomy blood from the upper compartment to combine with venous return blood passing into said flexible bag.

30. The device of claim 7 further comprising:
a first tube connecting the cardiotomy blood outlet of the upper compartment to the blood inlet of the flexible bag such that filtered cardiotomy blood will flow from the upper compartment into the flexible bag within said lower compartment.

31. The device of claim 7 wherein said flexible bag comprises an elongate bag and wherein said blood inlet is formed below the top end of the bag and said blood outlet is formed near the bottom end of the bag.

32. The device of claim 31 wherein a minimum operational blood level within the lower compartment is known and wherein said flexible bag is positioned within the lower compartment such that the blood outlet of the flexible bag is below the known minimum operational blood level within the lower compartment.

33. A blood reservoir device for receiving, filtering and combining cardiotomy blood and venous return blood in an extracorporeal blood oxygenation circuit, said device comprising:
a rigid housing defining an upper compartment and a lower compartment therewithin;
a cardiotomy blood inlet and a cardiotomy blood outlet formed in the upper compartment;
a cardiotomy blood filter disposed within the upper compartment between the cardiotomy blood inlet and cardiotomy blood outlet such that blood entering the cardiotomy blood inlet will pass through the filter prior to exiting the upper compartment through the cardiotomy blood outlet;
a flexible bag disposed within the lower compartment, said flexible bag having a top end, a bottom end, a blood inlet, a blood outlet and a microporous screen element positioned between the blood inlet and the blood outlet such that blood entering the flexible bag through the blood inlet will pass through the microporous screen element prior to exiting the flexible bag through the blood outlet;
the blood inlet of the flexible bag being fluidly connected to the cardiotomy blood outlet of the upper compartment and concurrently fluidly connectable to a source of venous return blood such that filtered cardiotomy blood from the upper compartment may combine with venous return blood within the flexible bag; and a blood outlet port formed in said lower compartment to permit blood which exits the flexible bag and collects outside of said flexible bag to subsequently pass out of said lower compartment.

34. The device of claim 33 wherein the cardiotomy filter element disposed within said upper compartment comprises:

a porous filter element formed around and defining an inner blood receiving space adjacent said cardiotomy inlet such that blood flowing in the cardiotomy inlet will enter the inner blood receiving space and will subsequently pass outwardly through said porous filter element.

35. The device of claim 34 wherein said porous filter element comprises a polyester felt material.

36. The device of claim 33 further comprising:

a defoamer element mounted within the upper chamber and interposed between the cardiotomy blood inlet and the cardiotomy blood outlet such that cardiotomy blood entering the upper chamber through the cardiotomy inlet will pass through the defoamer element prior to exiting the upper chamber through the cardiotomy blood outlet.

37. The device of claim 36 wherein said defoamer element comprises a quantity of porous foam material containing a chemical antifoam agent.

38. The device of claim 36 wherein said defoamer element and said porous filter element are both configured and disposed about an inner blood receiving space adjacent said cardiotomy blood inlet such that cardiotomy blood flowing in the cardiotomy blood inlet will initially pass into said inner blood receiving space and will subsequently pass outwardly through the defoamer element and through the porous filter element.

39. The device of claim 36 wherein said defoamer element has a pore size of approximately 400-1800 microns.

40. The device of claim 36 wherein said defoamer element is formed of porous polyurethane foam.

41. The device of claim 33 wherein the flexible bag is positioned within the lower compartment such that blood exiting the outlet of the flexible bag will enter the lower compartment, outside of the flexible bag prior to passing out of the lower compartment through said blood outlet port.

42. The device of claim 33 wherein a minimum operational blood level in the lower compartment is known and wherein:

the flexible bag is positioned within the lower compartment such that the blood outlet of the flexible bag is beneath the minimum blood level in said lower compartment.

43. The device of claim 33 further comprising a plate mounted in the lower compartment to which said flexible bag is mounted.

44. The device of claim 43 wherein said plate is positioned in spaced relation to a first portion of said rigid housing and wherein said flexible bag is positioned between said plate and said first portion of the rigid housing such that expansion of said flexible bag is limited to the space existing between said plate and said portion of said rigid housing.

45. The device of claim 44 wherein the first portion of the rigid housing is the rearward wall of the lower compartment such that the bag is disposed between said plate and said rearward wall.

46. The device of claim 33 wherein the microporous screen element has a pore size of approximately 40-200 microns.

47. The device of claim 33 wherein:

the top end of said flexible bag is open; and a second porous defoamer element is disposed within the top end of flexible bag such that foam rising within the flexible bag will contact said defoamer element prior to flowing out of the open top end of the flexible bag.

48. The device of claim 47 wherein said second porous defoamer element comprises:

at least a first mass of porous foam material positioned inside the flexible bag, adjacent the open top end thereof.

49. The device of claim 47 wherein said second porous defoamer element further comprises:

at least a second mass of porous foam material disposed outside of said flexible bag near the open top end thereof.

50. The device of claim 33 wherein the portion of said rigid housing defining said lower compartment comprises a forward wall and a rearward wall, opposing said forward wall, said forward wall and said rearward wall being closest to one another at the bottom end of said lower compartment and diverging away from one another thereabove.

51. The device of claim 50 wherein said device is mountable on a stand above a generally horizontal underlying floor such that the forward wall of the lower compartment is disposed at an angle of about 60-85 degrees relative to the underlying floor.

52. The device of claim 51 wherein the forward wall of the lower compartment is disposed at an angle of approximately 70 degrees relative to the underlying floor.

53. The device of claim 33 wherein said rigid housing is formed of clear plastic.

54. The device of claim 53 wherein a gradient scale is formed on the forward wall of the lower compartment to permit measurement of the level of blood within said lower compartment.

55. The device of claim 33 wherein said flexible bag comprises an elongate bag and wherein said blood inlet is formed below the top end of the bag and said blood outlet is formed near the bottom end of the bag.

56. The device of claim 26 wherein:

the blood outlet of the flexible bag is located such that blood passing out of said blood outlet will collect inside of said lower compartment and outside of said flexible bag.

57. The device of claim 56 wherein a minimum operational blood level within the lower compartment is known and wherein said flexible bag is positioned within the lower compartment such that the blood outlet of the flexible bag is below the known minimum operational blood level within the lower compartment.

58. The device of claim 33 wherein a bifurcated connector assembly having a first tubular portion and a second tubular portion is fluidly connected to the blood inlet of the flexible bag and wherein the first tubular portion of the bifurcated connector assembly is fluidly connected to the cardiotomy blood outlet of the upper chamber and wherein the second tubular portion of the bifurcated connector assembly is connected to a venous blood return tube.

59. The device of claim 58 wherein said connector assembly comprises:

a central hub portion having a hollow inner bore and an inner wall formed therewithin to divide said inner bore into a first inner chamber and a second inner chamber;

said first inner chamber being in fluid communication with said first tubular portion and said second tubular portion being in fluid communication with said second inner chamber; and both the first and second inner chambers of the connector assembly being fluidly connected to the inlet of the flexible bag so that cardiotomy blood and venous return blood may separately enter the flexible bag through the respective first and second inner chambers of the connector assembly.

* * * * *